United States Patent [19]
Elloy et al.

[11] 4,030,143
[45] June 21, 1977

[54] ENDOPROSTHETIC BONE JOINT DEVICES

[75] Inventors: Martin Arthur Elloy, Liverpool; Frank Howard Beddow, West Kirby, both of England

[73] Assignee: National Research Development Corporation, London, England

[22] Filed: Jan. 29, 1976

[21] Appl. No.: 653,524

[30] Foreign Application Priority Data
Jan. 31, 1975 United Kingdom ............ 04421/75

[52] U.S. Cl. .................................. 3/1.91; 3/1.912; 128/92 C
[51] Int. Cl.² .......................................... A61F 1/24
[58] Field of Search ........................ 3/1, 1.9–1.913; 128/92 C, 92 CA

[56] References Cited
UNITED STATES PATENTS

| | | | |
|---|---|---|---|
| 3,842,442 | 10/1974 | Kolbel | 3/1.91 |
| 3,863,273 | 2/1975 | Averill | 3/1.91 |
| 3,916,451 | 11/1975 | Buechel et al. | 3/1.91 |

FOREIGN PATENTS OR APPLICATIONS
1,362,187 7/1974 United Kingdom ............. 3/1.91

Primary Examiner—Ronald L. Frinks
Attorney, Agent, or Firm—Cushman, Darby & Cushman

[57] ABSTRACT

A ball-and-socket joint prosthesis developed for the shoulder has one component in the form of a ball connected through a neck to a stem, a first cup engaged with the ball in a snap fit which is held captive by a first clip connected round the cup, and a second cup releasably engaged around the remainder of the ball. The second cup is slotted from its rim to accommodate the first component neck and so predetermine the relative positions of these parts, and the second cup rim is complementary with that of the first cup to predetermine the relative positions of the cups around the ball. The resultant assembly therefore fixes the relative positions of the one component and first cup to facilitate securement of these parts, while keeping the articular surfaces free of cement, and the second cup is removed after securement to leave a stable captive ball-and-socket joint.

8 Claims, 17 Drawing Figures

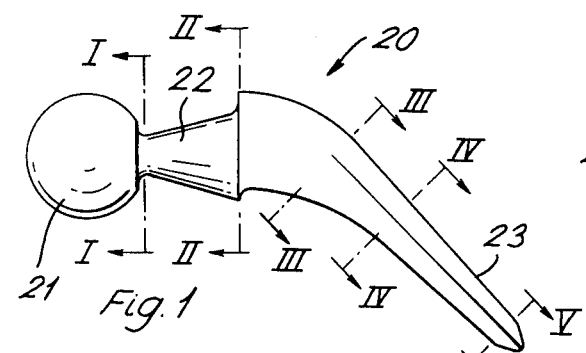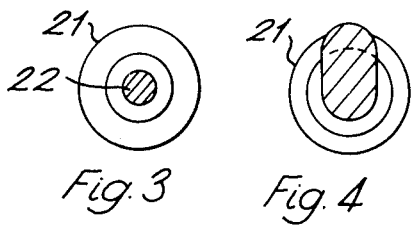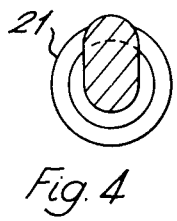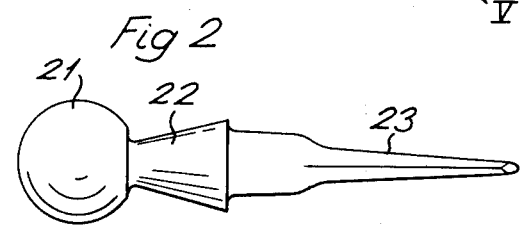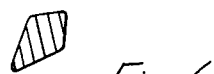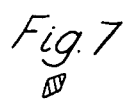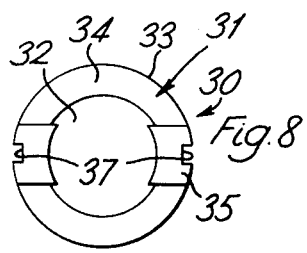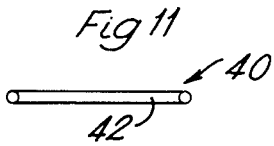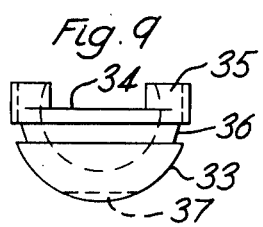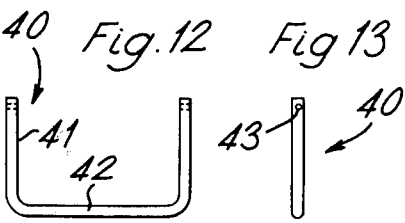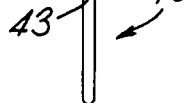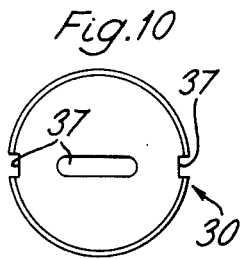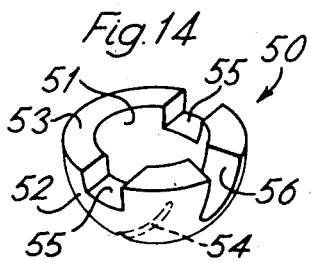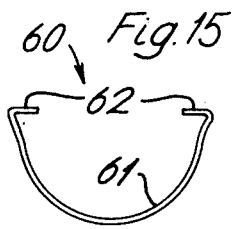

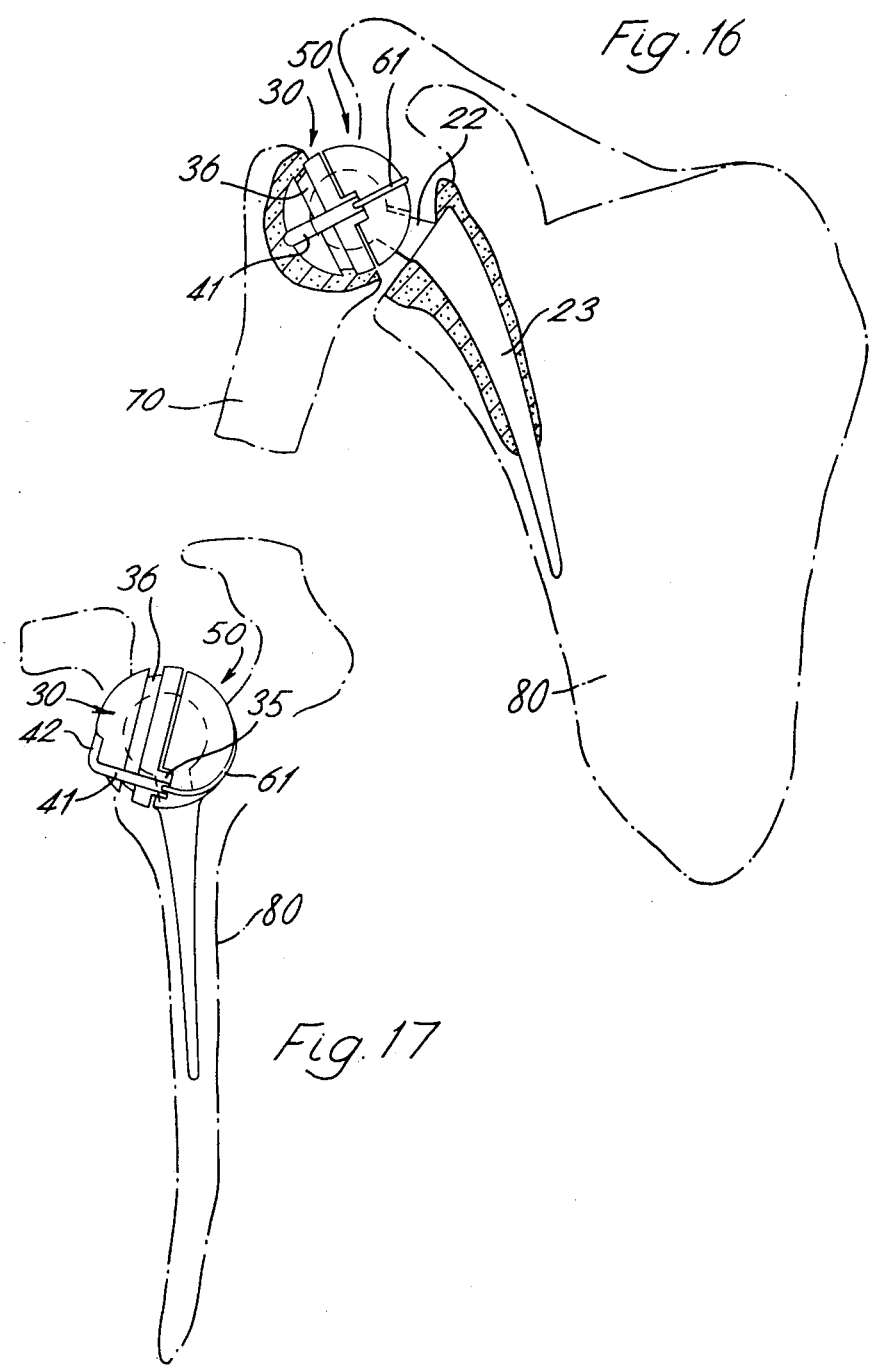

ENDOPROSTHETIC BONE JOINT DEVICES

This invention concerns endoprosthetic bone joint devices and more particularly, but not exclusively, such devices for the shoulder joint.

The shoulder joint has, of all the major joints, the greatest range of movement and two thirds of this movement occurs at the ball-and-socket joint between the humerus and scapula. This last joint has been the subject of various proposals for endoprosthetic devices, but none so far appear to satisfy adequately the basic requirements for such a device. These requirements can be summarized as:

1. Involve a simple operative procedure causing minimal trauma.
2. Allow sound fixation, even in badly eroded bone.
3. Provide correct anatomical function with a full range of movement.
4. Entail innate stability to compensate for loss of natural constraints.

Requirements (3) and (4) are inter-related because early mobilization of the joint is required to ensure a full range of movement, but this is only possible if the prosthesis has inherent stability. Lack of stability allows dislocation with consequent disruption and subsequent stiffening of the newly forming fibrous capsule and other healing soft tissue, and such damage not only extends the recovery time but results ultimately in a reduced range of movement.

The prior proposals mentioned above have led to three basic types of device, as follows:

a. An Anatomical type in which the humeral head is replaced by a component of the same geometry, commonly of metal and usually secured by way of an intramedullary stem, while the scapular glenoid is substituted by a correspondingly shallow lining of metal or plastics material secured by short members penetrating the scapular. This type gives normal function but does nothing to rectify lost joint integrity due to degenerated musculature and ligaments.

b. A small head type which is similar to the anatomical type but employs a smaller headed humeral component bearing with a hemispherically cupped scapular component. This deeper cup goes some way to improving joint stability, but invariably the centre of rotation is unnaturally close to the scapula and restricts the range of movement by improper relationship with muscle attachments and also by contact between the humerus and the acromion and caracoid processes of the scapula.

c. A reverse anatomical type which is also similar to the anatomical type but with a hemispherically cupped humeral component and a ball scapular component. This gives normal joint function together with the improved stability of a more deeply cupped component, but the reversed geometry places a much greater strain on the scapular component fixation. This last deficiency is particularly significant since, in rheumatoid arthritic joints, bone erosion can leave little material for fixation of scapular components. Indeed, in some cases the glenoid cavity hardly exists and the remaining joint function is exercised between the humeral head and the acromion and caracoid processes.

An object of the present invention is to provide an endoprosthetic device which can better satisfy the above requirements, and such a device comprises: a first component in the form of a substantially spherically shaped ball connected through a necked portion to an elongate stem; a second component in the form of a cup having an interior surface with complementary shaping to said ball, said interior surface extending over an area less than that of said ball but greater than a hemisphere, said cup having at least one resilient rim portion to allow engagement of said ball therein, and said cup having an exterior surface with a relieved configuration; and a third component in the form of a clip adapted to extend around said exterior surface, to engage with said relieved configuration, and to hold each said rim portion against movement allowing disengagement of said ball from said cup.

In the more general use of the proposed device, the ball and cup are engaged, this engagement is held against dislocation by engagement of the clip with the cup, and the overall assembly is implanted with the first component being secured by way of its stem in one bone of the relevant joint and with the cup and clip being secured in the other bone of the joint with use of cement. This last step involves bonding the clip with the exterior surface of the cup by mutual encapsulation in cement, and so the ball and cup engagement is firmly secured against dislocation.

As intimated by the initial introduction above, the present device has been developed for application to the shoulder joint and for this purpose it it intended that a reversed anatomical configuration be used with the first component stem cemented in a channel formed in the thickened bone along the lateral margins of the scapula to afford fixation adequate to meet the higher stresses of this configuration. Also it is preferred for this purpose that the cup has main interior surface area which is no greater than hemispherical, but is extended by two diametrally-opposed secondary surface areas provided by respective lug-like integral formations at the rim of the cup.

It is further preferred that the proposed device additionally comprises:

a fourth component in the form of a cup having a rim substantially complementary to that of the first-mentioned cup, and having an interior surface engageable around the ball in diametrically opposed location to the first cup with the two cup rims engaged, the second-mentioned cup being slotted from its rim to accommodate the necked portion of said first component. This second cup can be held in position by a fifth component in the form of a further clip engageable around the second cup and with at least one of the first cup and the first-mentioned clip. Alternatively, the second cup can be held in position by way of a mutual snap fit with another component of the device. For example, the two cups can be formed to effect a mutual snap fit around the ball, conveniently by appropriate shaping of the above-mentioned lug formations in the first cup and the complementary formations in the second cup. In another such arrangement, which is to be employed in a current clinical trial, the second cup snaps around the necked portion of the first component.

This addition serves to constrain the ball between the two cups so that the components are held in a consistent positional relationship during fixation, whereafter the second cup is removed to allow articulation. The second cup also services to maintain the articulatory surfaces free from cement.

It is also possible that the first clip may be omitted and the first cup be simply engaged by a snap fit, in similar manner to the second clip and cup.

A fuller understanding of the invention will be gained by consideration of the following description of the presently preferred shoulder joint embodiment thereof with reference to the accompanying drawings, in which:

FIGS. 1 and 2 are mutually perpendicular side views of the first component of the relevant embodiment, FIGS. 3 to 7 are sectional views respectively taken at 1—1 to V—V in FIG. 1, FIGS. 8 to 10 respectively illustrate the associated second component in one end view, a side view, and the opposite end view, FIGS. 11 to 13 respectively illustrate the associated third component in three mutually perpendicular elevation views, FIGS. 14 and 15 respectively illustrate associated fourth and fifth components in perspective and side elevation views, and FIGS. 16 and 17 respectively illustrate in anterior and lateral views the components when assembled and located relative to the scapula and humerus.

The illustrated first component is of integral metal construction denoted generally at 20 and comprises a spherically shaped ball 21 leading through a necked portion 22 to a stem 23. The ball 21 is of about 20 mm diameter and is connected to the narrower end of the necked portion 22, the latter being of frustoconical shape. The stem 23 is of tapered form connected in off-set overlapping manner with the necked portion 22 at their wider ends. Also the stem is longitudinally curved over its wider end portion so that its narrower end portion has its longitudinal axis angled at about 45° to that of necked portion 22, the latter axis being, in turn, diametrally located relative to the ball 21. It will also be seen that the wider, curved end portion of the stem 23 has a sectional shaping which is of generally round-ended, rectangular form as shown by FIG. 4, while the remainder of the stem is of relatively reduced, tapering form with generally diamond sectional shape as shown by FIGS. 5 to 7.

The illustrated second component is the 'first' cup, of integral plastics material construction, and denoted generally at 30. The cup 30 has a main body portion 31 of hemispherical shape and uniform thickness to define interior and exterior surfaces 32 and 33 of which the former has the same diameter as the ball 20, and a planar rim surface 34. Two like, diametrally-opposed lugs 35 extend integrally from the rim surface 34, the interior and exterior surfaces 32 and 33 continuing smoothly across these lugs with respectively spherical and cylindrical shaping.

The remaining features of the cup 30 comprise grooves formed in the exterior surface 33. A first such groove 36 is of annular form located parallel to the rim surface 34, while three further grooves 37 are disposed orthogonally to groove 36 in the medial plane of the cup relative to the lugs 35. Two of the grooves 37 extend similarly over respective ones of the lugs 35 to communicate with the groove 36, and the third groove 37 extends across the region of the exterior surface 33 furthest from the rim surface 34.

The illustrated third component is the 'first' clip and is denoted generally at 40. This clip comprises a metal rod formed to a rectangular U-shape with arms 41 and base 42. The clip rod is of circular sectional shape having a diameter equal to the width of grooves 37. Also, the clip arms 41 are each formed with a bore 43 passing diametrally therethrough adjacent its free end, these bores being axially aligned.

The illustrated fourth component is the 'second' cup and is of integral plastics material construction denoted generally at 50. The cup 50 is of similar shape to the first cup 30 in having hemispherical interior and exterior surfaces 51 and 52 of like diameter to those of cup 30, and a planar rim surface 53. However, the exterior surface 52 has only a single groove 54 located similarly to the third one of grooves 37 in the first cup, and the rim surface 53 has no lugs. Instead the rim surface is formed with three notches. Two of these notches 55 are complementary to the lugs 35, and the third notch 56 is generally complementary to the cross-sectional shape of the necked portion 22 adjacent the ball 21.

The illustrated fifth component is the 'second' clip and is denoted generally at 60. This clip 60 is of metal wire formed to comprise a main body portion 61 of generally semi-circular shape, and two radially-inwardly-projecting, free-end portions 62. The wire of clip 60 has circular sectional shape of like diameter to the first clip bores 43 and the second cup groove 54, and the diameter of the main body portion is substantially equal to that of the exterior surface 52 of the second cup.

In assembly of the illustrated embodiments, the ball 21 is snapped into the first cup 30, the material of the cup 30 being of such resilience and the lugs being of such dimensions as to allow this engagement. This ball-and-cup engagement is then rendered captive by locating the first clip 40 around the cup 30 with the clip arms 41 engaged in the grooves 37 extending over the lugs 35, and with the clip base 42 engaged in the remaining groove 37. Again, the clip 40 is resilient to allow its location as just described, but the resultant force required to remove the ball from the clipped first cup is clearly significantly greater than that to engage the ball in the cup without its clip. Thereafter, the first and second components are relatively positioned, by mutual articulation of the ball and first cup, so that the second cup 50 can be located over the ball with the cup rim surfaces 34 and 53 abutted, with the lugs 35 received in the notches 55, and with the necked portion 22 accommodated in the notch 56. This location of the second cup is then held by engagement of the second clip 60 around the second cup with the main body portion of this clip received in the second cup groove 54, and with end portions 62 of the second clip sprung into the bores 43 of the first clip. In addition, or alternatively, the second cup can be held in location by a snap fit as mentioned earlier.

The components are intended to be used in the assembled form just described and a preferred operative procedure involves a standard anterior approach in the delto-pectoral groove, with the incision being extended by dividing the anterior third of the deltoid from its scapular insertion. The subscapularis is divided and the joint opened through an anterior incision in the capsule. The articular surfaces are assessed and the head of the humerus removed through the anatomical neck. The glenoid fossa is deepened using a small gouge and Volkmann spoon and the deepening is extended down the auxiliary border of the scapula using a finger down this border as a director. The track is completed using the stem of a trial prosthesis. Using a gouge and spoon, a bed is then prepared in the humerus for the first cup and clip of the prosthesis and a trial reduction made. When sufficient bone has been removed from the scapula and humerus to allow satisfactory reduction with the trial prosthesis, this is removed and bone cement pressed into the stem bed in the scapula and the stem of the prosthesis to be implanted is pressed firmly into position and held until the cement has set. A further trial reduction of the humerus to the latter prosthesis is made before pressing cement in the humeral bed and reducing the humerus to receive the first cup and clip in full external rotation. This reduction is held until the cement has set, surplus cement being removed during this time. The second cup and clip are then removed and the range of articulation checked before closing the wound in layers with drainage.

The assembled device is shown relative to the humerus 70 and scapula 80 in FIGS. 16 and 17, the former being an anterior view but with the humeral components misplaced for clarity of illustration of the overall assembly, and the latter being a lateral view with the assembly in full external rotation relative to the scapula.

The advantages of the illustrated embodiment and its use as just described are that: it is appropriate to employ a simple operative procedure requiring no special instrumentation and causing no undue trauma; a good range of articulation is possible, with up to 135° abduction and 110° flexion: inherent joint stability is provided, allowing early mobilization with speedy recovery and reduced likelihood of subsequent decrease in range of movement; sound scapular fixation can be effected even in cases with severe rheumatoid arthritic erosion; consistent relative positioning of the prosthesis components is maintained during fixation; cement is restrained from access to the articular surfaces; and the implanted first clip serves as a radiological marker for the first cup.

In conclusion it is to be noted that these advantages are not exclusive to the illustrated embodiment, but can be provided by other forms of the invention within the scope of the appendant claims. Also, while the invention has been developed in relation to the shoulder joint, the invention can find advantageous application in other joints, such as the hip, where ball-and-socket prosthetic devices are employed.

We claim:

1. An endoprosthetic bone joint device comprising:
    a first component in the form of a substantially spherically shaped ball connected through a necked portion to an elongate stem;
    a second component in the form of a cup having an interior surface with complementary shaping to and engaged with said ball, said interior surface extending over an area less than that of said ball but greater than a hemisphere, said cup having at least one resilient rim portion to allow engagement of said ball therein, and said cup having an exterior surface with a relieved configuration;
    a third component in the form of a clip extending around said exterior surface, engaged with said relieved configuration, and holding each said rim portion captively engaged with said ball; and
    a fourth component in the form of a second cup having a rim substantially complementary to that of the first-mentioned cup, having an interior surface engaged around said ball in diametrally opposed location to said first cup with the two cup rims engaged, being slotted from its rim to accommodate said necked portion, and being releasably held in a predetermined positional relationship with said first and second components.

2. A device according to claim 1 wherein said second component cup has two of said rim portions comprising respective diametrally opposed lugs, the main body of the interior surface of such cup being no greater than hemispherical but being extended beyond a hemisphere by said lugs.

3. A device according to claim 2 wherein said relieved configuration comprises grooves extending circumferentially around said exterior surface and along said lugs, and said clip comprises a U-shaped structure seated in said grooves and embracing said lugs.

4. A device according to claim 1 for use as a humeroscapular replacement with said first and second components respectively adapted as scapular and humeral components, said first component having said necked portion extending substantially diametrally from said ball, and said stem being of tapered, longitudinally curved form with its wider end connected to said necked portion in transversely off-set manner.

5. A device according to claim 1 wherein the exterior surface of said second cup has a relieved configuration, and said device comprises a second clip engaging such configuration and releasably connected with one of said second and third components.

6. A device according to claim 1 wherein said second cup is held in a mutual snap fit with one of said first and second components.

7. A device according to claim 6 wherein said first and fourth components effect a mutual snap fit between said necked portion and said slot accommodating the same.

8. An endoprosthetic bone joint device comprising:
    a first component in the form of a ball connected through a neck to the wider end of a tapered stem;
    a first cup engaged with said ball by a mutual snap fit to form a ball and socket joint;
    and a second cup held in releasable engagement with said ball, said second cup being slotted from its rim to accommodate said neck and predetermine the relative positions of said second cup and said ball, and the rim of said first and second cups being complementary and abutted to predetermine the positions of said cups relative to each other.

* * * * *